US011432776B2

(12) United States Patent
Bastide et al.

(10) Patent No.: US 11,432,776 B2
(45) Date of Patent: Sep. 6, 2022

(54) MEDICAL DEVICE ADMINISTRATION AND INTERACTION

(71) Applicant: International Business Machines Corporation, Armonk, NY (US)

(72) Inventors: Paul R Bastide, Ashland, MA (US); Fang Lu, Billercia, MA (US); Ishwarya Rajendrababu, Hoboken, NJ (US); Sathyanarayanan Srinivasan, Cambridge, MA (US)

(73) Assignee: International Business Machines Corporation, Armonk, NY (US)

( * ) Notice: Subject to any disclaimer, the term of this patent is extended or adjusted under 35 U.S.C. 154(b) by 172 days.

(21) Appl. No.: 16/440,285

(22) Filed: Jun. 13, 2019

(65) Prior Publication Data

US 2020/0390401 A1 Dec. 17, 2020

(51) Int. Cl.
*G16H 40/40* (2018.01)
*A61B 5/00* (2006.01)
(Continued)

(52) U.S. Cl.
CPC .......... *A61B 5/7282* (2013.01); *A61B 5/0533* (2013.01); *A61B 5/082* (2013.01);
(Continued)

(58) Field of Classification Search
CPC ..... A61B 5/7282; A61B 5/0533; A61B 5/082; A61B 5/4839; A61B 5/165; G16H 10/60;
(Continued)

(56) References Cited

U.S. PATENT DOCUMENTS 5,167,506 A 12/1992 Kilis et al.
8,948,935 B1 2/2015 Peeters et al.
(Continued)

FOREIGN PATENT DOCUMENTS

WO 2014023422 A1 2/2014

OTHER PUBLICATIONS

Kanitkar Anjali, Effectiveness of employing multimedia principles in the design of computer-based math tutorials for students with learning disabilities, year 2010, 245 pages.*
(Continued)

*Primary Examiner* — Jason S Tiedeman
*Assistant Examiner* — Liza Tony Kanaan
(74) *Attorney, Agent, or Firm* — Patterson + Sheridan, LLP (57) ABSTRACT

The present disclosure provides for medical device administration and interaction by identifying a medical event affecting a first individual, a medical device associated with treating the medical event, and an initial attentiveness level of an administering individual; outputting a tutorial for how to use the medical device to treat the medical event with a first control level, wherein the first control level based on the initial attentiveness level of the administering individual; and in response to receiving a triggering event while outputting the tutorial: determining a current attentiveness level for the administering individual; and in response to the current attentiveness level indicating a change from the initial attentiveness level, adjusting the tutorial based on a second control level, different than the first control level, based on the change from the initial attentiveness level.

20 Claims, 7 Drawing Sheets

(51) Int. Cl.
*A61B 5/0533* (2021.01)
*G16H 10/60* (2018.01)
*G16H 40/67* (2018.01)
*A61B 5/08* (2006.01)

(52) U.S. Cl.
CPC ............ *G16H 10/60* (2018.01); *G16H 40/40* (2018.01); *G16H 40/67* (2018.01)

(58) Field of Classification Search
CPC ........ G16H 40/40; G16H 40/67; G16H 20/10; A61M 15/00; A61M 15/009; A61M 2205/505
See application file for complete search history.

(56) References Cited

U.S. PATENT DOCUMENTS

| | | | |
|---|---|---|---|
| 2009/0109399 A1* | 4/2009 | Severns | A61B 3/09 351/210 |
| 2009/0253982 A1* | 10/2009 | Wang | A61B 5/4884 600/419 |
| 2011/0226242 A1 | 9/2011 | Von Hollen et al. | |
| 2011/0253139 A1 | 10/2011 | Guthrie et al. | |
| 2012/0115122 A1* | 5/2012 | Bruce | G09B 5/12 434/323 |
| 2012/0136270 A1 | 5/2012 | Leuthardt et al. | |
| 2013/0110565 A1* | 5/2013 | Means, Jr. | G06Q 10/063 705/7.11 |
| 2016/0007935 A1* | 1/2016 | Hernandez | A61B 5/024 600/595 |
| 2017/0281712 A1* | 10/2017 | Rhodes | A61P 43/00 |
| 2017/0290979 A1 | 10/2017 | Gordon et al. | |
| 2017/0357776 A1* | 12/2017 | Baker | G09B 19/0053 |
| 2018/0182475 A1* | 6/2018 | Gossler | G16H 50/50 |
| 2019/0042699 A1 | 2/2019 | Bastide et al. | |
| 2019/0148025 A1* | 5/2019 | Stone | G16H 20/17 705/2 |
| 2019/0198166 A1* | 6/2019 | Errico | G07F 17/0092 |
| 2019/0240842 A1* | 8/2019 | Hsu | G06F 3/017 |
| 2020/0082327 A1* | 3/2020 | Arefieg | G16H 40/20 |
| 2020/0357497 A1* | 11/2020 | Kamber Todd | G06F 21/60 |
| 2020/0398112 A1* | 12/2020 | Lu | A63B 22/02 |

OTHER PUBLICATIONS

Kanitkar Anjali, Effectiveness of employing multimedia principles in the design of computer-based math tutorials for students with learning disabilities, year 2010, 245 pages (Year: 2010).*

* cited by examiner

MEDICAL DEVICE ADMINISTRATION AND INTERACTION

BACKGROUND

The present invention relates to medical devices, and more specifically, to monitoring the administration and interaction with the medical device during a medical event to improve the administration of the medical device and the resolution of the medical event. As various medical devices are designed to be administered during an acute medical event, the person using the medical device may be under greater mental stress. This mental stress may be compounded if the medical device is unfamiliar to the administrating individual, or if treatment deviates from a typical administration, which may lead to more stress and a non-optimal administration of the medical device—wasting medication, requiring multiple applications, not delivering treatment to the correct location, non-timely treatment of the medical event, etc.

SUMMARY

According to one embodiment of the present invention, a method for medical device administration and interaction is provided, the method including: identifying a medical event affecting a first individual, a medical device associated with treating the medical event, and an initial attentiveness level of an administering individual; outputting a tutorial for how to use the medical device to treat the medical event with a first control level, wherein the first control level based on the initial attentiveness level of the administering individual; and in response to receiving a triggering event while outputting the tutorial: determining a current attentiveness level for the administering individual; and in response to the current attentiveness level indicating a change from the initial attentiveness level, adjusting the tutorial based on a second control level, different than the first control level, based on the change from the initial attentiveness level.

According to one embodiment of the present invention a system for medical device administration and interaction is provided, the system including: a processor; and a memory storage device, including processor-executable instructions that when performed by the processor perform an operation comprising: identifying a medical event affecting a first individual, a medical device associated with treating the medical event, and an initial attentiveness level of an administering individual; outputting a tutorial for how to use the medical device to treat the medical event with a first control level, wherein the first control level based on the initial attentiveness level of the administering individual; and in response to receiving a triggering event while outputting the tutorial: determining a current attentiveness level for the administering individual; and in response to the current attentiveness level indicating a change from the initial attentiveness level, adjusting the tutorial based on a second control level, different than the first control level, based on the change from the initial attentiveness level.

According to one embodiment of the present invention a computer program product including a computer-readable storage medium having computer-readable program code embodied therewith that is executable by one or more computer processors to provide for medical device administration and interaction is provided to identify a medical event affecting a first individual, a medical device associated with treating the medical event, and an initial attentiveness level of an administering individual; output a tutorial for how to use the medical device to treat the medical event with a first control level, wherein the first control level based on the initial attentiveness level of the administering individual; and in response to receiving a triggering event while outputting the tutorial: determine a current attentiveness level for the administering individual; and in response to the current attentiveness level indicating a change from the initial attentiveness level, adjust the tutorial based on a second control level, different than the first control level, based on the change from the initial attentiveness level.

DETAILED DESCRIPTION

The present disclosure provides systems and methods to improve the usage and administration of medical devices by monitoring the physical and mental states of one or more of the administering individual and the treated individual during administration of the device. As used herein, the administering individual (also referred to as the treating individual) is the person who is using the medical device, and the treated individual (also referred to as the affected individual) is experiencing the medical event. Although many of the examples given herein indicate a separate person administering the medical device from the person undergoing the medical event, in some embodiments the medical device is self-administered where the administering individual and the treated individual are the same person. For example, a person experiencing a medical event of bronchial constriction (e.g., due to asthma), may use an inhaler or be assisted by a third party in using an inhaler to counteract the bronchial constriction. Additionally, although most of the examples given herein indicate that the treated individual undergoing the medical event is a human, in other embodiments a non-human animal may be the treated individual.

By monitoring the usage of the medical device in conjunction with the mental state, including the level of concentration, level of confidence, level of agitation, etc., of the administering individual, a tutorial (or other operating instructions) for the medical device can be adapted to the attentiveness level that is appropriate for the current mental state of the administering individual. Additional data on the physical state of the treated individual, the administering individual, and the medical device can be collected to further adapt provision of the operating instructions.

Figure 1A:
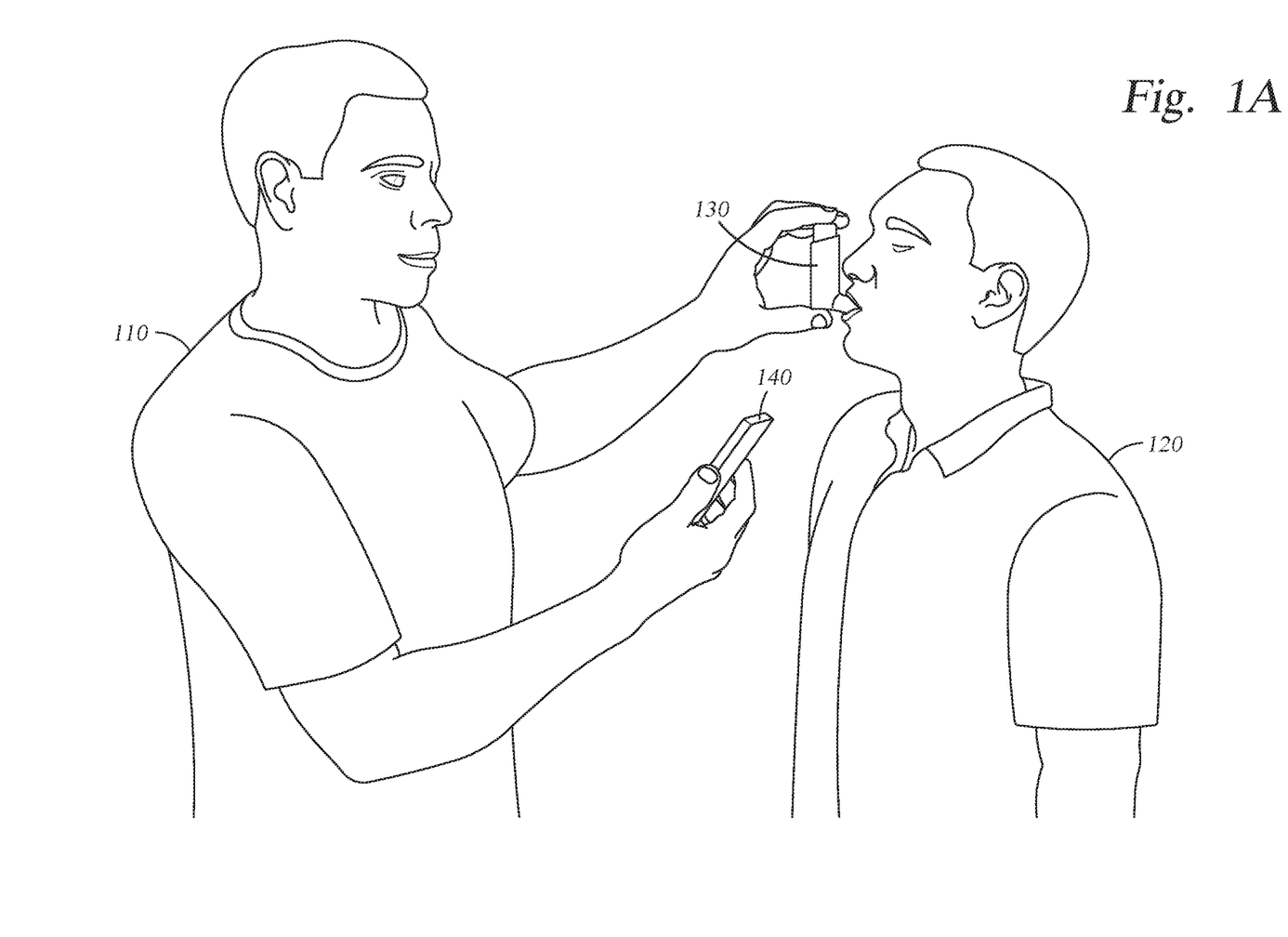
FIGS. 1A and 1B illustrate scenes in which a medical event is treated, according to embodiments of the present disclosure.
Figure 1B:
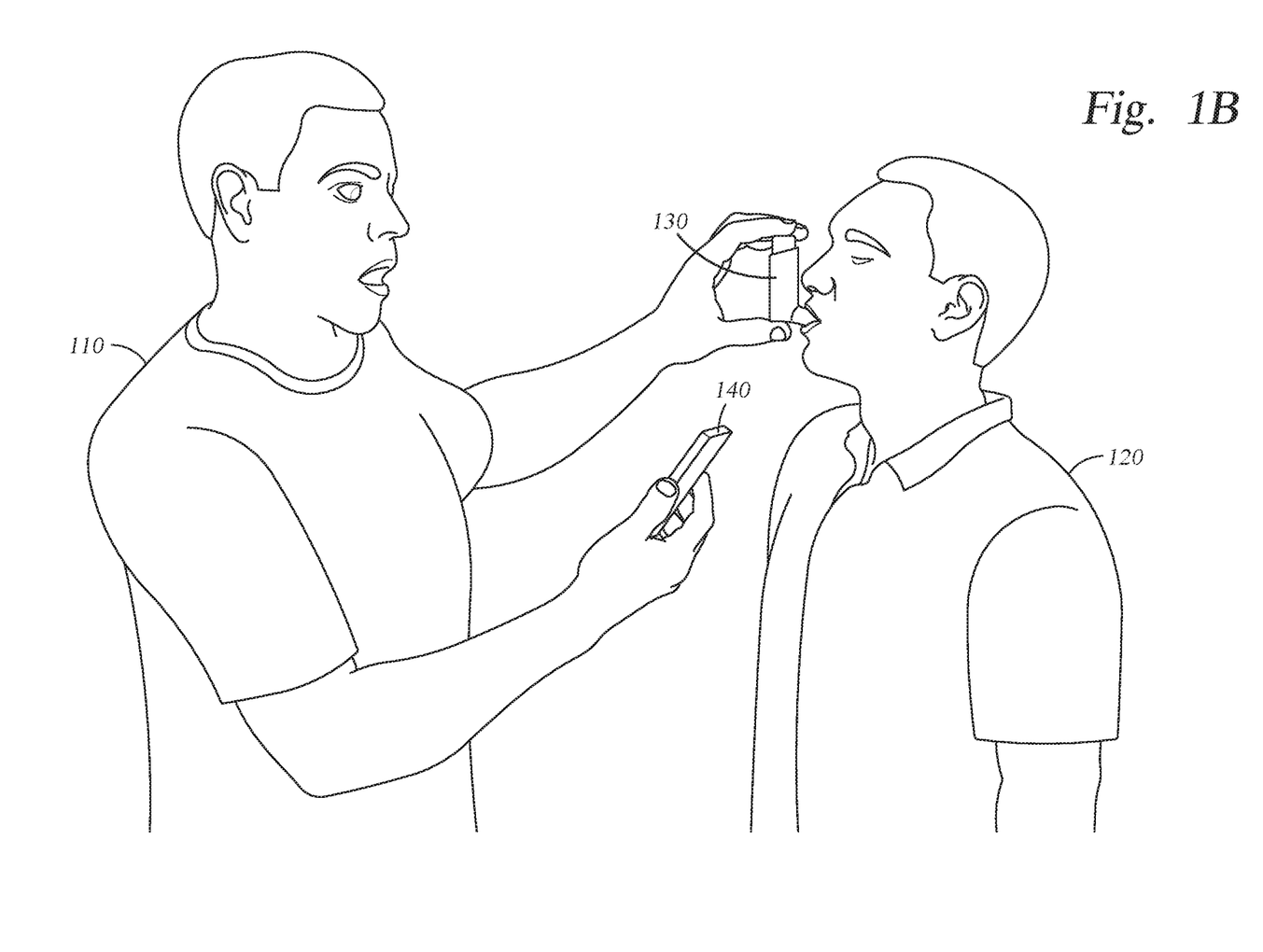

Consider, for example, the scenes illustrated in FIGS. 1A and 1B, in which an administering individual 110 is helping a treated individual 120 use a medical device 130 (e.g., an inhaler) according to instructions provided by a monitoring device 140 of a smart phone. If the administering individual 110 is observed to have a calm and collected mental state, and the medical device 130 is observed to be progressing through the operating instructions, as is shown in FIG. 1A, the monitoring device 140 may provide operating instructions in a first manner (e.g., as an overview). However, if the monitoring device 140 observes the administering individual 110 to have a panicked or disoriented mental state, as is shown in FIG. 1B, or the medical device 130 to not be progressing through the operating instructions, the monitoring device 140 may adjust the operating instructions to provide a more detailed or more controlled manner to provide the treatment (e.g., a step-by-step process). As will be appreciated, an administering individual 110 who is calm, attentive, and familiar with the medical device 130 may be slowed down by the provision of a highly-detailed set of instructions, whereas an administering individual 110 who is not calm, attentive, or familiar with the medical device 130 may be slowed down or confused by a less comprehensive set of instructions. Accordingly, the present disclosure monitors the current mental state of an administering individual 110 to provide effective instruction adapted to the attentiveness level associated with that mental state to quickly, accurately, and efficiency administer the medical device 130 for treating a medical event.

Although FIGS. 1A and 1B illustrate the medical device 130 as an inhaler (e.g., for delivering asthma medication or bronchodilators), other examples of medical devices 130 include, but are not limited: auto-injectors (e.g., for epinephrine in allergic reactions), defibrillators, insulin pumps, tourniquets, intravenous drips, and the like.

Although FIGS. 1A and 1B illustrate the monitoring device 140 as a smart phone, other computing devices (e.g., tablets, laptops, smart watches, an integrated computer in the medical device 130) may be used as the monitoring device 140 in other embodiments. Example computing hardware for the monitoring device 140 (and computerized portion of the medical device 130) are discussed in greater detail in regard to FIG. 4.

Figure 2A:
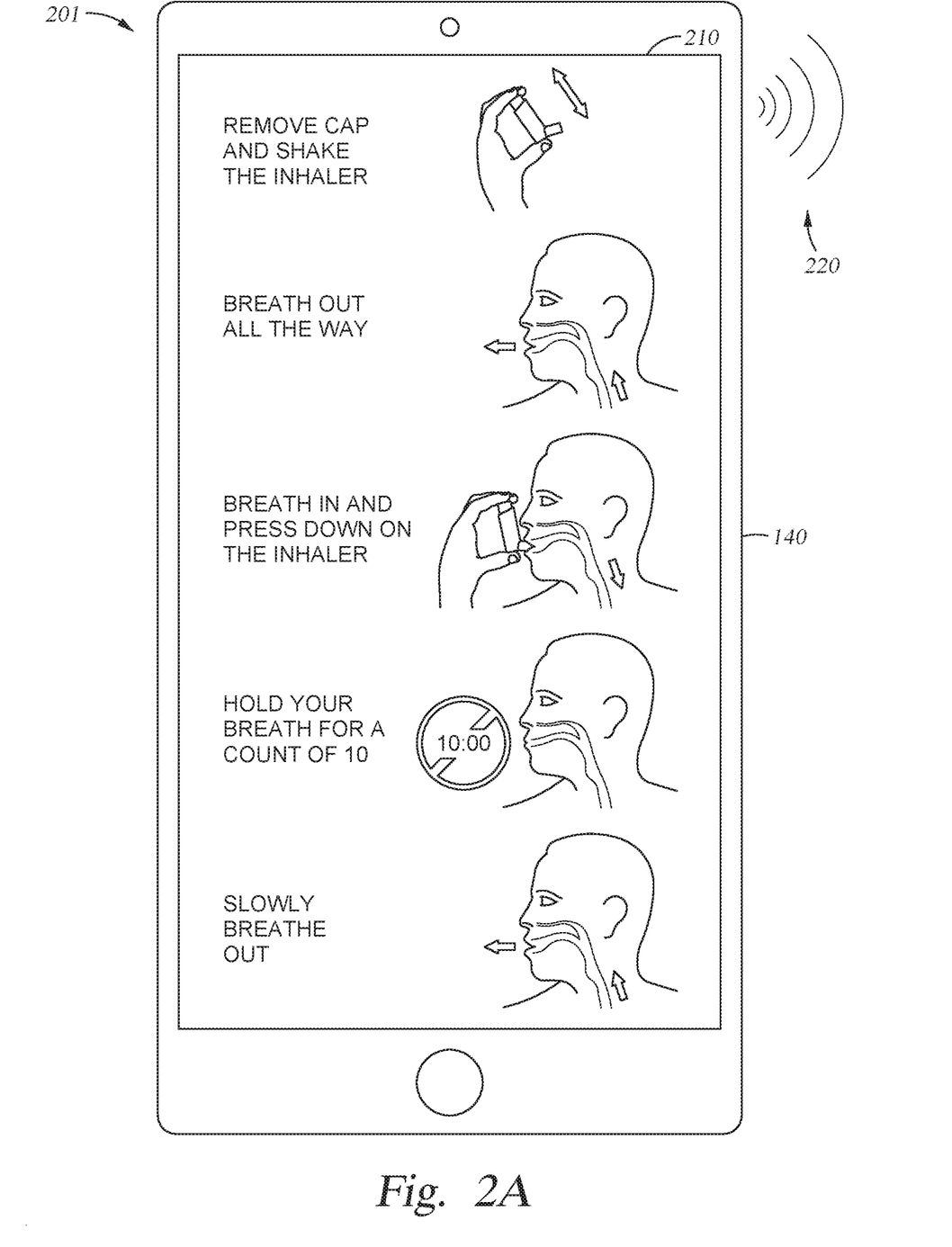
FIG. 2A-2F illustrate instructions for treating a medical event, according to embodiments of the present disclosure.

FIGS. 2A-2F illustrate instructions for treating the medical event illustrated in FIGS. 1A and 1B, as may be presented to the administering individual 110 by the monitoring device 140. FIG. 2A illustrates a first tutorial 201, as may be provided by the monitoring device 140 in FIG. 1A, and FIGS. 2B-2F illustrates a second tutorial 202, as may be provided by the monitoring device 140 in FIG. 1B. The first tutorial 201 provides a higher level set of instructions than the second tutorial 202, which provides a more-detailed and/or more-controlled set of instructions for addressing the same medical event.

FIG. 2A provides the first tutorial 201 in a Graphical User Interface (GUI) 210 detailing the steps that the administering individual 110 is to take when using the medical device 130. For example, a set of written and pictographic instructions are provided to remind the administering individual 110 of each of the individual instructions for how the medical device 130 is to be used in treating the medical event. Additionally, in various embodiments, the first tutorial 201 may include an associated sound clip 220 that provides audio instructions for the individuals to follow. In various embodiments, the monitoring device 140 may provide the first tutorial 201 using both the GUI 210 and the sound clip 220, only the GUI 210, or only the sound clip 220.

FIGS. 2B-2F provide the second tutorial 202 in a series of GUIs 210a-e that detail individual steps of how to use the medical device 130 to the administering individual 110. Each of the GUIs 210a-e are presented sequentially to the administering individual 110 (and the treated individual 120) to walk the individuals through how to use the medical device 130 in treating the medical event. In some embodiments, the instructions presented in the first tutorial 201 may be identical to those presented in the second tutorial 202, but spread over more GUIs 210. In other embodiments, the instructions presented in the second tutorial 202 may include additional steps (or breakdowns of steps included in the first tutorial 201) to provide greater detail in how to address the medical event than is included in the first tutorial 201.

The monitoring device 140 determines which instruction set to provide based on the mental state of the administering individual 110 and additional data related to the mental or physical state of the treated individual 120. In some embodiments, the administering individual 110 may override the determination made by the monitoring device 140 of which instruction set to provide and manually select which instruction set to receive. Additional input related to the mental state or the physical state of the treated individual 120 or the physical state of the medical device 130 may be provided to or collected by the monitoring device 140 to determine when to insert additional steps or remove steps from the instruction set. For example, in the first GUI 210a of FIG. 2B, the instruction to "remove the cap from the inhaler" may be excluded when the monitoring device 140 determines that the cap has already been removed (or is otherwise absent) from the medical device 130.

Figure 2B:
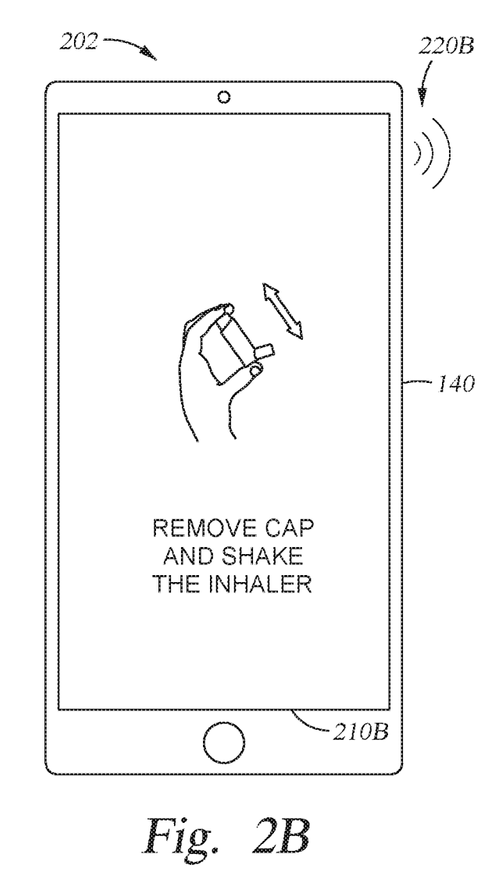
Figure 2C:
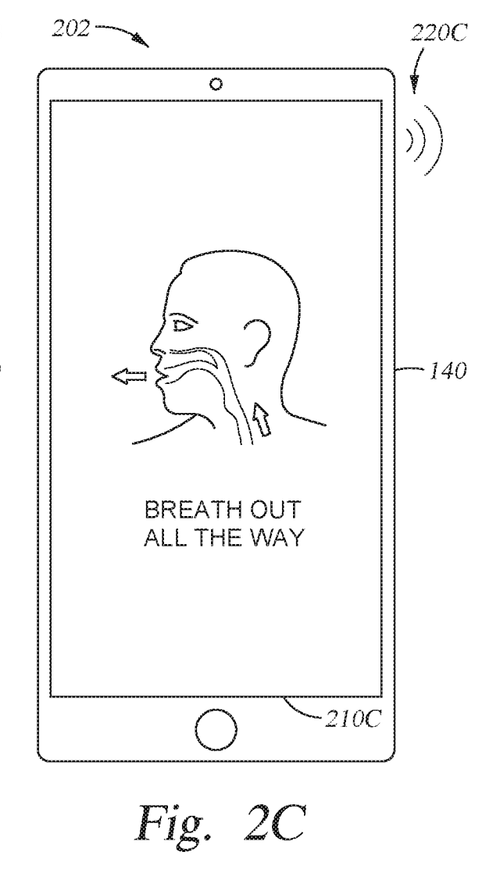
Figure 2D:
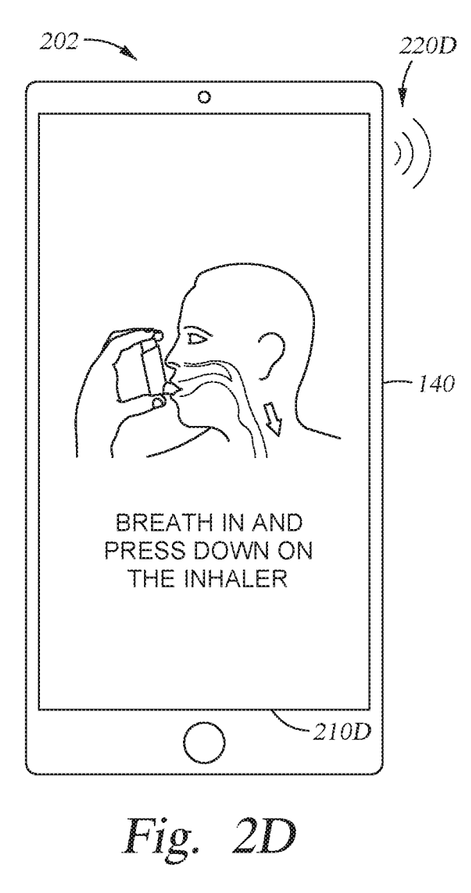
Figure 2E:
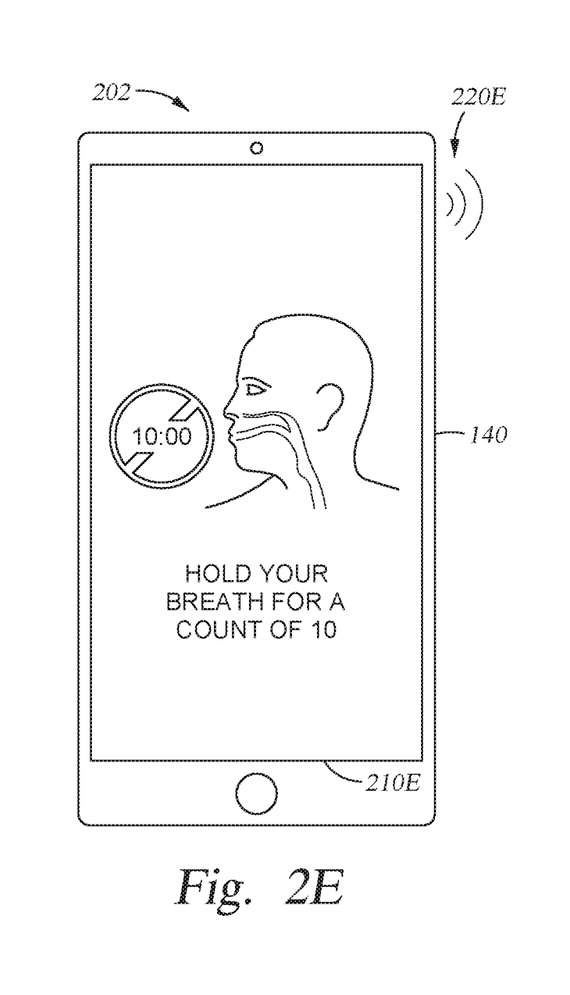
Figure 2F:
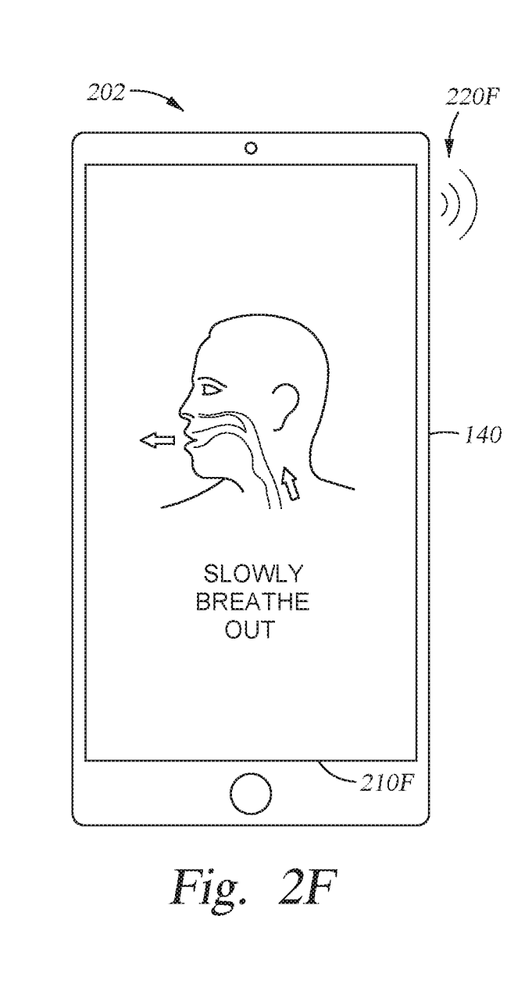

In the second tutorial 202, each step is presented in a controlled manner to guide the administering individual 110 through the treatment process. For example, the monitoring device 140 may display the first GUI 210a and play an associated first sound clip 220a to provide the administering individual 110 with instructions to "remove the cap and shake the inhaler". Once the monitoring device 140 detects a triggering event, the monitoring device 140 advances to the next step to display the second GUI 210b and play a second sound clip 220b. The monitoring device 140 may thus confirm each step is being performed before advancing to a subsequent step to guide the administering individual 110 through the treatment process.

Depending on the triggering event, the monitoring device 140 may repeat the current step (e.g., replaying the associated sound clip 220), advance to a next step in a sequence, return to an earlier step in the sequence, or adjust which tutorial 201/202 is provided to the individuals. Triggering events may be generally classified into three categories: instructional, physical, and mental.

Examples of instructional triggering events include: a manual commands (e.g., a button push of either a software button in the associated GUI 210 or a physical button on the monitoring device 140), voice commands (e.g., "acknowledged," "next step please," "repeat that," "I do not understand"), and the like. Examples of physical triggering events include: movement of the medical device 130 (e.g., based on camera images, an accelerometer/gyroscope), sounds from the environment (e.g., a discharging sound from the medical device 130), and the like. Examples of mental triggering events include determinations of the current mental state of the administering individual 110 has changed by one or more biological features that are indicative of focus, understanding, or clarity of thought in the administering individual 110.

The monitoring device 140 observes, via one or more cameras and one or more microphones, the administering individual 110 to determine the mental state of the administering individual 110. The monitoring device 140 compares the images and audio patterns received from the administering individual 110 against various models to determine one or more of: a facial expression indicative of a mental state (e.g., concentrating, assured, confused, panicked, delirious), an eye gaze/focus (e.g., paying attention to the treated individual 120, the medical device 130, or the monitoring device 140), a vocal pattern indicative of a mental state, body language (e.g., trembling, clenched jaw, hunched shoulders) indicative of a mental state, and the like. The monitoring device 140 may monitor the mental state of the administering individual 110 by one or more of: a breathing rate, vocal patterns (e.g., pitch, inter-word cadence, intra-word cadence, volume), facial expression, eye focus, steadiness (e.g., measured by an accelerometer in a device held by the administering individual 110), and the like. The models may be specific to a particular administering individual 110 or generalized to a population to link various mental states. The models may include various types of machine learning models (e.g., a neural network) trained to identify a mental state based on the data provided by the monitoring device 140 related to the administering individual 110. The model may be run locally on the monitoring device 140 or may be run on a remote system hosting the model in communication with and using the monitoring device 140 as an endpoint.

Additional stimuli from the environment, the medical device 130, and the treated individual 120 may also be collected by the monitoring device 140 via the cameras, microphones, contact sensors, and positional sensors to supplement the information about the mental state of the administering individual 110. In some embodiments, the instructional and physical triggering events may be used to determine a mental triggering event. For example, the monitoring device 140 can recognize receiving several instructional commands to "repeat" an individual instruction or several instructions in the tutorial 201/202 as a mental triggering event that the administering individual 110 is confused. In another example, the monitoring device 140 can recognize the lack of feedback from the medical device 130 to be a mental triggering event that the administering individual 110 is having difficulty in using the medical device 130 as instructed. In a further example, the monitoring device 140 can recognize a misapplied or out of order performance of the instructions as a mental triggering event.

Consider, for example, a monitoring device 140 providing the first tutorial 201 and monitoring the mental state of the administering individual 110 that determines that the administering individual 110 is confused or disoriented. Based on the determined confusion/disorientation, the monitoring device 140 adjusts the first tutorial 201 to the second tutorial 202, which breaks the steps of the first tutorial 201 into individual segments to guide the administering individual 110 through. If the monitoring device 140 detects additional or increasing confusion/disorientation from the administering individual 110 at a given instruction in the second tutorial 202, the monitoring device 140 may provide further details or control for that given instruction. For example, when the administering individual 110 is presented with the third GUI 210c to "breathe in and press down on the inhaler," and the monitoring device 140 identifies the administering individual 110 is having difficulties in performing the instruction, the monitoring device 140 may further adjust the second tutorial 202 to help guide the administering individual 110 through a difficult or confusing portion of the instructions.

Consider, in another example, a monitoring device 140 providing the second tutorial 202 and monitoring the mental state of the administering individual 110 that determines that the administering individual 110 is neither confused nor disoriented, but has a clear and focused attentiveness level (and may be impatient to progress through the instructions). Based on the determined clarity/focus, the monitoring device 140 adjusts the second tutorial 202 to the first tutorial 201, which provides the administering individual 110 an overview of how to use the medical device 130 rather than individual steps. In this way, the monitoring device 140 may provide more detailed or more controlled provision of the instructions to portions of the tutorial posing particular problems to the user, and provide less detailed or less controlled provision of the instructions to those portions of the tutorial not posing difficulty to the user; thus speeding up treatment of the medical event by providing an appropriately matched level of detail and control for providing the tutorial based on the user's attentiveness level in the observed mental state.

Although the examples provided herein discuss a first tutorial 201 and a second tutorial 202, in various embodiments, more than two tutorials are contemplated, and tutorials may be developed on a continuum of levels of detail and control (e.g., from basic overview instructions to methodical step-by-step instructions).

Figure 3:
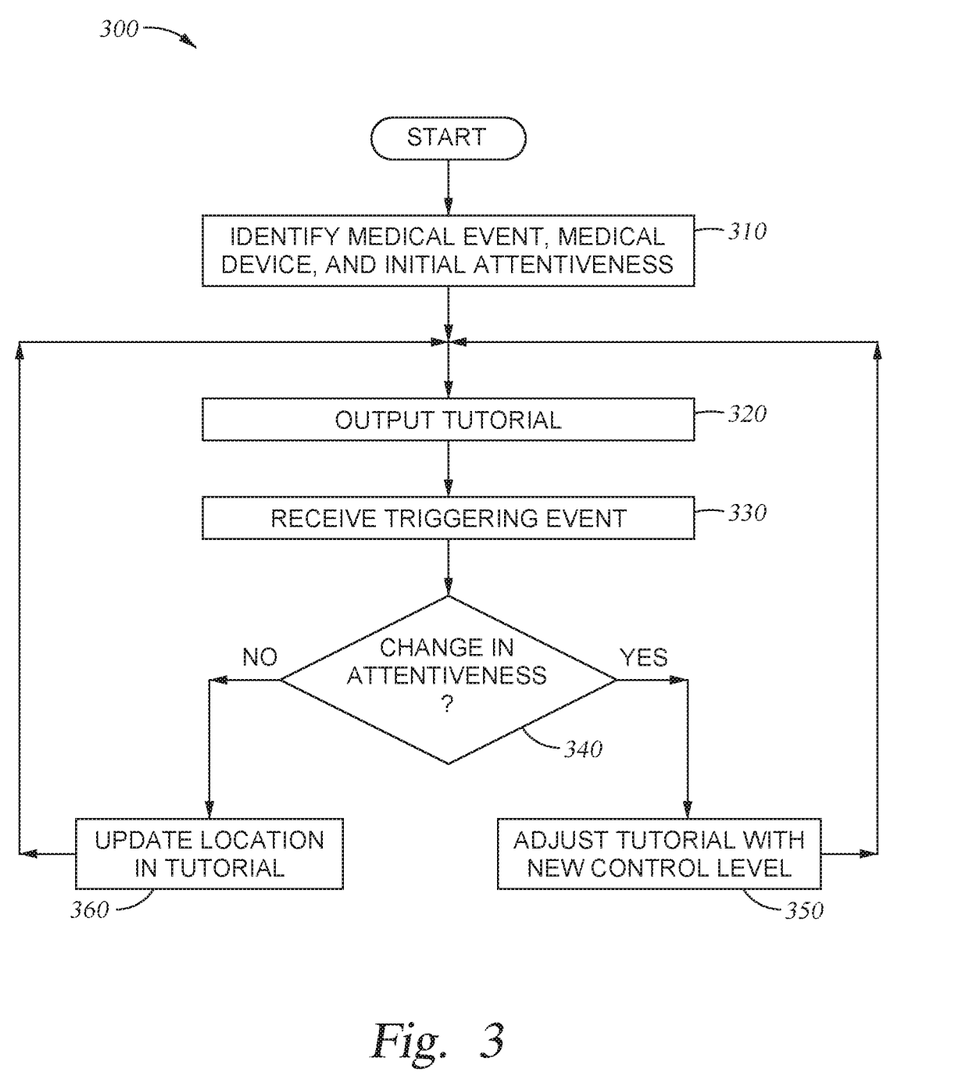
FIG. 3 is a flowchart of a method for managing medical device administration and interaction according to the mental state and associated attentiveness level of an administering individual, according to embodiments of the present disclosure.

FIG. 3 is a flowchart of a method 300 for managing medical device administration and interaction according to the attentiveness level of an administering individual 110. Method 300 begins with block 310, where the monitoring device 140 identifies a medical event affecting an affected individual 120, a medical device 130 associated with treating the medical event/the affected individual 120, and an initial mental state of an administering individual 110. In various embodiments, the affected individual 120 and the administering individual 110 are the same individual, but may be different individuals on other embodiments.

In some embodiments, the monitoring device 140, or an application selected thereon, is associated with a particular medical device 130 or medical event, and the medical device 130 or medical event is identified based on the monitoring device 140 or application selected to provide the tutorial. In some embodiments, the monitoring device 140 receives input from the environment related to the physical condition of the affected individual 120 (e.g., breathing rate, galvanic skin response, temperature, facial expression) to determine the medical event and the appropriate/associated medical device 130 to treat that medical event.

The monitoring device 140 may also access a medical record for the affected individual 120. The medical record may include a prescription for the medical device 130, and instructions for the use thereof, and may indicate for how long the affected individual 120 has been subject to or at risk for this medical event (e.g., in a medical file for a person or a species-specific veterinary record for a non-human animal). In some embodiments, the monitoring device 140 uses the medical record (and the physical condition) for the affected individual 120 to determine whether the medical event is a routine condition that has been experienced by the affected individual 120 for at least a predetermined threshold number of times or length of time. Alternatively to a routine condition, the monitoring device 140 may determine that the medical event is an emergent condition that affects the affected individual 120 infrequently or unpredictably, or that has been experienced for less than the predetermined threshold number of times or length of time. The routine/emergent nature of the medical event may affect the mental state of the administering individual 110, such that medical events that are routine are treated as requiring a control state that is less detailed/controlled than medical events that are emergent.

The monitoring device 140 may determine the initial mental state (and subsequent mental states at later times)

based on one or more of: a mood of the administering individual 110 based on facial and body language analysis, a breathing rate via a gyroscope or a microphone, speech patterns, gaze of the administering individual, a skin temperature or conductivity, and the like.

At block 320, the monitoring device 140 outputs a tutorial for how to use the medical device 130 to treat the medical event with a first control level. The first control level is based on the initial mental state of the administering individual 110, and specifies how the tutorial is to be provided to the administering individual 110. For example, the control level for a calm and collected individual with a high level of attentiveness may be associated with an overview tutorial, such as that illustrated in FIG. 2A, whereas the control level for a nervous or distracted individual with a low level of attentiveness may be associated with a step-by-step tutorial, such as that illustrated in FIGS. 2B-2F.

At block 330, the monitoring device 140 receives a triggering event while outputting the tutorial. In various embodiments, the triggering event is received as an instructional event, a physical event, or a mental event. The monitoring device 140 may detect an instructional event via a physical interface (e.g., a button), a software-defined interface (e.g., a button in a GUI) as a command from the administering individual 110 to change the control level or position in the tutorial. The monitoring device 140 may detect a physical event as a change in the environment affecting the affected individual 120 or the medical device 130 (e.g., the affected individual 120 performing an instructed action, the medical device 130 being deployed, a position of the medical device 130 relative to the individuals) via various sensors. The monitoring device 140 may detect a mental event as a change in the mental state and attentiveness level of the administering individual 110 by changes in one or more of: a mood of the administering individual 110 based on facial and body language analysis, a breathing rate via a gyroscope or a microphone, speech patterns, gaze of the administering individual, a skin temperature or conductivity, and the like. The change in attentiveness level may be indicated also by instructional events to repeat instructions, physical events that indicate non-compliance with provided instructions or delays in compliance with the provided instructions, and the like.

At block 340, the monitoring device 140 determines whether the administering individual 110 has experienced a change in mental state and attentiveness level. When the monitoring device 140 has determined a change in mental state and attentiveness level, method 300 proceeds to block 350. When the monitoring device has not determined a change in mental state or attentiveness level, method 300 proceeds to block 360.

At block 350, the monitoring device 140 adjusts the tutorial with a new control level based on the current mental state and attentiveness level of the administering individual 110. The new control level may increase the level of detail and/or level of control for provision of the tutorial when the new mental state is less attentive, more confused/disoriented, more panicked, or otherwise indicating that the administering individual 110 is having difficulty following the tutorial. The new control level may decrease the level of detail and/or level of control for provision of the tutorial when the new mental state is more attentive, more assured, more calm, or otherwise indicating that the administering individual 110 can proceed more quickly. Compared to a lower level of detail or control, a higher level of detail or control may result in one or more of the following: providing instructions as separate steps rather than an overview, providing supplemental instructions, playing an audio clip, using a slower speed of provision of the tutorial, requiring more elaborate triggering events to advance to a subsequent instruction (e.g., a call-and-repeat trigger, where the user repeats the instructions aloud to advance), etc.

In some embodiments, the monitoring device 140 may also, in addition to or instead of changing the control level for the tutorial, adjust the provision of the tutorial on the monitoring device 140 by one or more of: increasing a volume of an audio device outputting the tutorial, changing a brightness of a display device outputting the tutorial, highlighting a portion of the tutorial, and adjusting a zoom or amount of the tutorial visible on the display device.

At block 360, the monitoring device 140 updates the location of the output of the tutorial based on the triggering event. In some embodiments, the triggering event concludes the administration of the medical device 130, and the monitoring device 140 accordingly concludes the output of the tutorial. In some embodiments, the triggering event signifies that the administering individual 110 is ready to proceed to a next step in the instructions or wishes to return to a previous instruction, and the monitoring device 140 accordingly navigates to next/previous instruction as indicated. Method 300 may then return to block 320.

Figure 4:
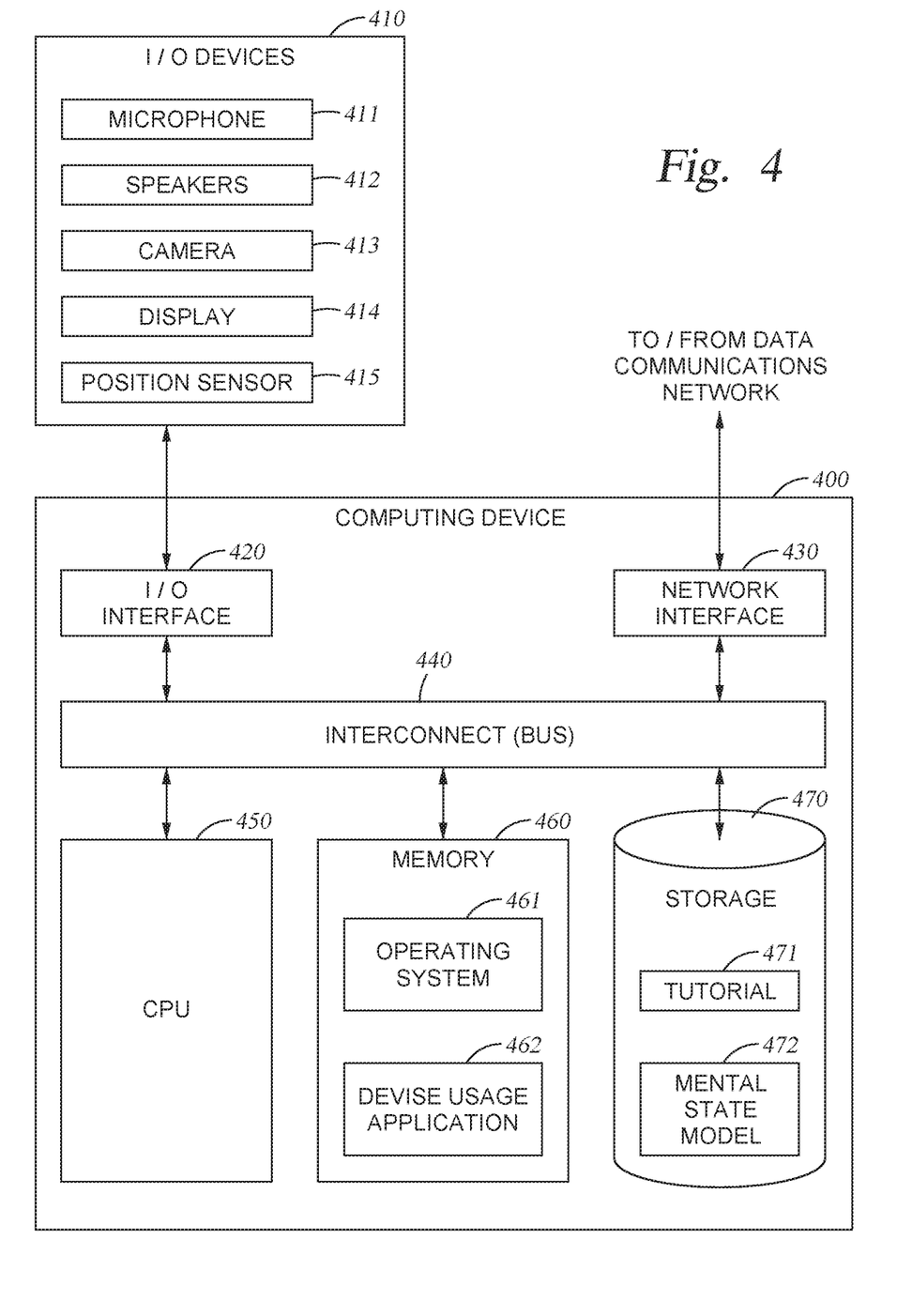
FIG. 4 illustrates a computing system, according to embodiments of the present disclosure.

FIG. 4 illustrates a computing system 400, which may be a personal computer, a laptop, a tablet, a smartphone, etc. As shown, the computing system 400 includes, without limitation, a central processing unit (CPU) 450, a network interface 430, an interconnect 440, a memory 460, and storage 470. The computing system 400 may also include an I/O device interface 420 connecting I/O devices 410 to the computing system 400. The I/O devices 410 include, but are not limited to, a microphone 411 for audio input, speakers 412 for audio output, a camera 413 for visual input, a display 414 for visual output, contact sensors 415 for measuring the body conditions of a person holding the contact sensors 415 (e.g., skin temperature, galvanic skin response measurements), and positional sensors 416 for spatial input (e.g., accelerometers, gyroscopes, magnetometers, Global Positioning System receivers).

The CPU 450 retrieves and executes programming instructions stored in the memory 460. Similarly, the CPU 450 stores and retrieves application data residing in the memory 460. The interconnect 440 facilitates transmission, such as of programming instructions and application data, between the CPU 450, I/O device interface 420, storage 470, network interface 440, and memory 460. CPU 450 is included to be representative of a single CPU, multiple CPUs, a single CPU having multiple processing cores, and the like. And the memory 460 is generally included to be representative of a random access memory. The storage 470 may be a disk drive storage device. Although shown as a single unit, the storage 470 may be a combination of fixed and/or removable storage devices, such as magnetic disk drives, flash drives, removable memory cards or optical storage, network attached storage (NAS), or a storage area-network (SAN). The storage 470 may include both local storage devices and remote storage devices accessible via the network interface 430.

Further, computing system 400 is included to be representative of a physical computing system as well as virtual machine instances hosted on a set of underlying physical computing systems. Further still, although shown as a single computing system, one of ordinary skill in the art will recognized that the components of the computing system 400 shown in FIG. 4 may be distributed across multiple computing systems connected by a data communications network. For example, the computing system 400 may represent components of the monitoring device 140 and the medical device 130 linked via a BLUETOOTH® or other communications protocol via associated network interfaces 430.

As shown, the memory 460 includes an operating system 461 (e.g., Microsoft's WINDOWS® Operating System) and a device usage application 462. The device usage application 462 includes programmatic instructions to perform the functionalities of the monitoring device 140 described herein. The device usage application 462 accesses one or more tutorials 471 (e.g., stored in the storage 470) for how to use an associated medical device 130, and selects which control level to provide the selected tutorial 471 at based on the output of a mental state model 472. The tutorial 471 may include a series of text, images (still or animated), and sound files to instruct a user in the proper usage of a medical device 130. The mental state model 472 receives data related to the administering individual 110 (e.g., facial expression, body language, gaze, vocal patterns) and the environment (e.g., the medical event, whether the medical device 130 is being used as instructed) and returns an attentiveness level associated with the mental state for the administering individual 110. The device usage application 462 receives the attentiveness level determination from the mental state model 472 and selects an associated control level for the tutorial 471, which is then output to the administering individual 110. Thus the device usage application 462 provides an appropriately detailed/controlled tutorial 471 for the mental state and attentiveness level of the administering individual 110 to quickly, accurately, and efficiency enable the administering individual 110 to use the medical device 130 for treating a medical event.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. A computer implemented method, comprising:
   performing by a computer operations comprising:
      identifying a medical event affecting a first individual, a medical device for treating the medical event, and an initial attentiveness level of an administering individual, wherein the initial attentiveness level of the administering individual is determined based at least in part on whether the first individual has experienced a medical condition associated with the medical event for a duration relative to a threshold length of time;
      controlling a monitoring device to display a tutorial for how to use the medical device to treat the medical event with a first control level, wherein the first control level is based on the initial attentiveness level of the administering individual; and
      in response to receiving a triggering event while outputting the tutorial, wherein the triggering event is detected using the monitoring device:
         determining a current attentiveness level for the administering individual;
         in response to the current attentiveness level indicating a reduction in attentiveness from the initial attentiveness level, adjusting the tutorial based on a second control level, different than the first control level, wherein:
            the second control level is based on the reduction in attentiveness from the initial attentiveness level;
            the second control level includes a greater number of sequentially provided instructions for the tutorial than the first control level includes; and
            each instruction at the second control level is provided at a slower speed than each instruction at the first control level which is provided at a faster speed; and
         controlling the monitoring device to display the tutorial at the second control level, comprising:
            sequentially outputting instructions via a sequence of interfaces, wherein the first control level provides instructions on a single interface;
            determining to output audio based on the second control level;
            supplementing the tutorial with additional information not provided using the first control level; and
            requiring the administering individual to provide more elaborate triggering event conditions, as compared to the first level of control, to advance to a subsequent instruction in the tutorial.

2. The computer implemented method of claim 1, wherein the first individual is the administering individual.

3. The computer implemented method of claim 1, wherein the first individual and the administering individual are two different human beings.

4. The computer implemented method of claim 1, wherein identifying the initial attentiveness level of the administering individual further comprises:
   determining, based on a physical condition and a medical record for the first individual who is different from the administering individual, whether the medical event is one of an emergent condition that has affected the first individual less than a threshold number of times or a routine condition that has affected the first individual at least the threshold number of times.

5. The computer implemented method of claim 4, wherein the first individual is a non-human animal and the administering individual is a human, wherein the medical record is a species-specific veterinary record.

6. The computer implemented method of claim 1, wherein identifying the initial attentiveness level of the administering individual further comprises:
monitoring a galvanic skin response in the administering individual;
monitoring a mood of the administering individual via facial analysis;
monitoring a breathing rate of the administering individual via a gyroscope;
monitoring speech patterns of the administering individual;
monitoring a direction of gaze of the administering individual;
monitoring a current position of the medical device relative to the first individual; and
monitoring a current deployment state of the medical device.

7. The computer implemented method of claim 1, the computer operations further comprising, in response to receiving the triggering event:
updating a location in the tutorial to a subsequent instruction in the tutorial.

8. The computer implemented method of claim 1, wherein the first control level differs from the second control level by at least one of:
a volume of the output audio;
a brightness of a display of the monitoring device;
a highlighted portion of the tutorial on the display of the monitoring device; or
a zoom amount of the tutorial on the display of the monitoring device.

9. A system, comprising:
a processor; and
a memory storage device, including processor-executable instructions that when performed by the processor perform an operation comprising:
identifying a medical event affecting a first individual, a medical device for treating the medical event, and an initial attentiveness level of an administering individual, wherein the initial attentiveness level of the administering individual is determined based at least in part on whether the first individual has experienced a medical condition associated with the medical event for a duration relative to a threshold length of time;
outputting a tutorial on a monitoring device for how to use the medical device to treat the medical event with a first control level, wherein the first control level based on the initial attentiveness level of the administering individual; and
in response to receiving a triggering event while outputting the tutorial, wherein the triggering event is detected using the monitoring device:
determining a current attentiveness level for the administering individual; and
in response to the current attentiveness level indicating a reduction in attentiveness from the initial attentiveness level, adjusting the tutorial based on a second control level, different than the first control level, wherein:
the second control level is based on the reduction in attentiveness from the initial attentiveness level;
the second control level includes a greater number of sequentially provided instructions for the tutorial than the first control level includes; and
each instruction at the second control level is provided at a slower speed or with more detail than each instruction at the first control level which is provided at a faster speed or with less detail; and
controlling the monitoring device to display the tutorial at the second control level, comprising:
sequentially outputting instructions via a sequence of interfaces, wherein the first control level provides instructions on a single interface;
determining to output audio based on the second control level;
supplementing the tutorial with additional information not provided using the first control level; and
requiring the administering individual to provide more elaborate triggering event conditions, as compared to the first level of control, to advance to a subsequent instruction in the tutorial.

10. The system of claim 9, wherein the first individual is the administering individual.

11. The system of claim 9, wherein identifying the initial attentiveness level of the administering individual further comprises:
determining, based on a physical condition and a medical record for the first individual who is different from the administering individual, whether the medical event is one of an emergent condition that has affected the first individual less than a threshold number of times or a routine condition that has affected the first individual at least the threshold number of times.

12. The system of claim 9, wherein identifying the initial attentiveness level of the administering individual further comprises:
monitoring a galvanic skin response in the administering individual;
monitoring a mood of the administering individual via facial analysis;
monitoring a breathing rate of the administering individual via a gyroscope;
monitoring speech patterns of the administering individual;
monitoring a direction of gaze of the administering individual;
monitoring a current position of the medical device relative to the first individual; and
monitoring a current deployment state of the medical device.

13. The system of claim 9, further comprising, in response to receiving the triggering event:
updating a location in the tutorial to a subsequent instruction in the tutorial.

14. The system of claim 9, wherein the first control level differs from the second control level by at least one of:
a volume of the output audio;
a brightness of a display of the monitoring device;
a highlighted portion of the tutorial on the display of the monitoring device; or
a zoom amount of the tutorial on the display of the monitoring device.

15. A computer program product comprising:
a computer-readable storage medium having computer-readable program code embodied therewith, wherein the computer-readable program code is executable by one or more computer processors to:
  identify a medical event affecting a first individual, a medical device for treating the medical event, and an initial attentiveness level of an administering individual, wherein the initial attentiveness level of the administering individual is determined based at least in part on whether the first individual has experienced a medical condition associated with the medical event for a duration relative to a threshold length of time;
  output a tutorial on a monitoring device for how to use the medical device to treat the medical event with a first control level, wherein the first control level based on the initial attentiveness level of the administering individual; and
  in response to receiving a triggering event while outputting the tutorial, wherein the triggering event is detected using the monitoring device:
    determine a current attentiveness level for the administering individual; and
    in response to the current attentiveness level indicating a reduction in attentiveness from the initial attentiveness level, adjust the tutorial based on a second control level, different than the first control level, wherein:
      the second control level is based on the reduction in attentiveness from the initial attentiveness level;
      the second control level includes a greater number of sequentially provided instructions for the tutorial than the first control level includes; and
      each instruction at the second control level is provided at a slower speed or with more detail than each instruction at the first control level which is provided at a faster speed or with less detail; and
    controlling the monitoring device to display the tutorial at the second control level, comprising:
      sequentially outputting instructions via a sequence of interfaces, wherein the first control level provides instructions on a single interface;
      determining to output audio based on the second control level;
      supplementing the tutorial with additional information not provided using the first control level; and
      requiring the administering individual to provide more elaborate triggering event conditions, as compared to the first level of control, to advance to a subsequent instruction in the tutorial.

16. The computer program product of claim 15, wherein the first individual is the administering individual.

17. The computer program product of claim 15, wherein to identify the initial attentiveness level of the administering individual the computer-readable program code is further executable by one or more computer processors to:
  determine, based on a physical condition and a medical record for the first individual who is different from the administering individual, whether the medical event is one of an emergent condition that has affected the first individual less than a threshold number of times or a routine condition that has affected the first individual at least the threshold number of times.

18. The computer program product of claim 15, wherein to identify the initial attentiveness level of the administering individual the computer-readable program code is further executable by one or more computer processors to:
  monitor a galvanic skin response in the administering individual;
  monitor a mood of the administering individual via facial analysis;
  monitor a breathing rate of the administering individual via a gyroscope;
  monitor speech patterns of the administering individual;
  monitor a direction of gaze of the administering individual;
  monitor a current position of the medical device relative to the first individual; and
  monitor a current deployment state of the medical device.

19. The computer program product of claim 15, wherein in response to receiving the triggering event the computer-readable program code is further executable by one or more computer processors to:
  update a location in the tutorial to a subsequent instruction in the tutorial.

20. The computer program product of claim 15, wherein the first control level differs from the second control level by at least one of:
  a volume of the output audio;
  a brightness of a display of the monitoring device;
  a highlighted portion of the tutorial on the display of the monitoring device; or
  a zoom amount of the tutorial on the display of the monitoring device.

* * * * *